(12) United States Patent
Steiner et al.

(10) Patent No.: US 8,152,846 B2
(45) Date of Patent: Apr. 10, 2012

(54) INSTRUMENTATION AND METHOD FOR REPAIR OF MENISCUS TISSUE

(75) Inventors: Anton J. Steiner, Wharton, NJ (US);
James Shock, Glen Rock, NJ (US);
John E. Barker, Effort, PA (US);
Gregory C. Fanelli, Daniville, PA (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 237 days.

(21) Appl. No.: 12/382,020

(22) Filed: Mar. 6, 2009

(65) Prior Publication Data
US 2009/0234452 A1 Sep. 17, 2009

Related U.S. Application Data

(60) Provisional application No. 61/064,461, filed on Mar. 6, 2008.

(51) Int. Cl.
*A61F 2/08* (2006.01)
(52) U.S. Cl. .................................................. 623/14.12
(58) Field of Classification Search ............... 623/14.12; 606/79–99
See application file for complete search history.

(56) References Cited

U.S. PATENT DOCUMENTS

| | | | | | |
|---|---|---|---|---|---|
| 1,384,330 | A | * | 7/1921 | Winfield | 81/490 |
| 4,052,753 | A | * | 10/1977 | Dedo | 623/14.12 |
| 4,150,675 | A | * | 4/1979 | Comparetto | 606/84 |
| 4,195,368 | A | * | 4/1980 | Patrichi | 623/14.12 |
| 4,325,373 | A | * | 4/1982 | Slivenko et al. | 606/96 |
| 4,344,193 | A | * | 8/1982 | Kenny | 623/14.12 |
| 4,421,112 | A | * | 12/1983 | Mains et al. | 606/88 |
| 4,481,947 | A | * | 11/1984 | Chester | 606/108 |
| 4,502,161 | A | * | 3/1985 | Wall | 623/14.12 |
| 4,627,425 | A | * | 12/1986 | Reese | 606/87 |
| 4,649,916 | A | * | 3/1987 | Frimberger | 606/1 |
| 4,703,751 | A | * | 11/1987 | Pohl | 606/62 |
| 4,711,238 | A | | 12/1987 | Cunningham | |
| 4,807,863 | A | * | 2/1989 | Yang | 269/153 |
| 4,813,413 | A | * | 3/1989 | Gray | 606/84 |
| 4,880,429 | A | * | 11/1989 | Stone | 623/14.12 |
| 4,919,667 | A | * | 4/1990 | Richmond | 623/14.12 |
| 4,985,031 | A | * | 1/1991 | Buss et al. | 606/82 |
| 5,035,699 | A | * | 7/1991 | Coates | 606/86 R |
| 5,067,964 | A | * | 11/1991 | Richmond et al. | 623/14.12 |
| 5,092,572 | A | * | 3/1992 | Litwak et al. | 5/600 |
| 5,092,894 | A | * | 3/1992 | Kenny | 128/898 |
| 5,100,409 | A | * | 3/1992 | Coates et al. | 606/88 |
| 5,139,520 | A | * | 8/1992 | Rosenberg | 606/87 |
| 5,163,665 | A | * | 11/1992 | Klearman | 269/280 |
| 5,171,322 | A | * | 12/1992 | Kenny | 623/14.12 |
| 5,246,444 | A | * | 9/1993 | Schreiber | 606/87 |
| 5,254,119 | A | * | 10/1993 | Schreiber | 606/87 |
| 5,263,498 | A | * | 11/1993 | Caspari et al. | 128/898 |
| 5,298,012 | A | * | 3/1994 | Handlos | 600/36 |
| 5,306,311 | A | * | 4/1994 | Stone et al. | 623/14.12 |
| 5,344,459 | A | * | 9/1994 | Swartz | 623/14.12 |
| 5,358,525 | A | * | 10/1994 | Fox et al. | 623/14.12 |
| 5,366,457 | A | * | 11/1994 | McGuire et al. | 606/86 R |
| 5,397,357 | A | * | 3/1995 | Schmieding et al. | 606/86 R |
| 5,413,579 | A | * | 5/1995 | Tom Du Toit | 606/87 |
| 5,415,663 | A | * | 5/1995 | Luckman et al. | 606/86 R |
| 5,423,827 | A | * | 6/1995 | Mumme et al. | 606/96 |

(Continued)

*Primary Examiner* — Alvin J Stewart
(74) *Attorney, Agent, or Firm* — John S. Hale; Gipple & Hale

(57) ABSTRACT

The invention is directed toward a method and instrumentation to replace a damaged human knee joint meniscus with an allograft meniscus. The implant has its bone base cut to a desired width in a workstation. The finished base is measured in the sizing groove of the sizing block for width and length. The tibia is then drilled with drill to the appropriate depth and length and groove is formed in the tibia with a tissue chisel so that the width is the same as the width of the bone base. The bone base is press fit into the tibia groove and may be secured with a bone screw.

14 Claims, 12 Drawing Sheets

U.S. PATENT DOCUMENTS

| | | | | |
|---|---|---|---|---|
| 5,449,360 A * | 9/1995 | Schreiber | | 606/87 |
| 5,466,243 A * | 11/1995 | Schmieding et al. | | 606/232 |
| 5,486,180 A * | 1/1996 | Dietz et al. | | 606/87 |
| 5,540,695 A * | 7/1996 | Levy | | 606/87 |
| 5,569,260 A * | 10/1996 | Petersen | | 606/88 |
| 5,571,109 A * | 11/1996 | Bertagnoli | | 606/86 A |
| 5,601,562 A * | 2/1997 | Wolf et al. | | 606/86 R |
| 5,613,969 A * | 3/1997 | Jenkins, Jr. | | 606/87 |
| 5,613,970 A * | 3/1997 | Houston et al. | | 606/88 |
| 5,620,448 A * | 4/1997 | Puddu | | 606/87 |
| 5,662,656 A * | 9/1997 | White | | 606/88 |
| 5,667,512 A * | 9/1997 | Johnson | | 606/88 |
| 5,681,320 A * | 10/1997 | McGuire | | 606/104 |
| 5,681,333 A * | 10/1997 | Burkhart et al. | | 606/148 |
| 5,683,400 A * | 11/1997 | McGuire | | 606/96 |
| 5,690,637 A * | 11/1997 | Wen et al. | | 606/88 |
| 5,693,056 A * | 12/1997 | Carls et al. | | 606/86 R |
| 5,702,462 A * | 12/1997 | Oberlander | | 128/898 |
| 5,709,689 A * | 1/1998 | Ferrante et al. | | 606/86 R |
| 5,713,897 A * | 2/1998 | Goble et al. | | 606/53 |
| 5,735,903 A * | 4/1998 | Li et al. | | 128/898 |
| 5,766,251 A * | 6/1998 | Koshino | | 623/11.11 |
| 5,785,714 A * | 7/1998 | Morgan et al. | | 606/86 R |
| 5,913,900 A * | 6/1999 | Stone | | 128/898 |
| 5,919,196 A * | 7/1999 | Bobic et al. | | 606/86 R |
| 5,957,926 A * | 9/1999 | Masini | | 606/87 |
| 5,968,050 A * | 10/1999 | Torrie | | 606/87 |
| 5,980,526 A * | 11/1999 | Johnson et al. | | 606/86 R |
| 6,063,088 A * | 5/2000 | Winslow | | 606/86 A |
| 6,102,954 A * | 8/2000 | Albrektsson et al. | | 623/20.32 |
| 6,152,928 A * | 11/2000 | Wenstrom, Jr. | | 606/232 |
| 6,176,880 B1 * | 1/2001 | Plouhar et al. | | 623/13.17 |
| 6,206,927 B1 * | 3/2001 | Fell et al. | | 623/20.29 |
| 6,264,657 B1 * | 7/2001 | Urbahns et al. | | 606/914 |
| 6,278,079 B1 * | 8/2001 | McIntyre et al. | | 219/121.67 |
| 6,468,314 B2 * | 10/2002 | Schwartz et al. | | 623/23.72 |
| 6,488,033 B1 * | 12/2002 | Cerundolo | | 128/898 |
| 6,558,421 B1 * | 5/2003 | Fell et al. | | 623/14.12 |
| 6,565,575 B2 * | 5/2003 | Lewis | | 606/99 |
| 6,629,997 B2 * | 10/2003 | Mansmann | | 623/14.12 |
| 6,632,246 B1 * | 10/2003 | Simon et al. | | 623/14.12 |
| 6,640,666 B2 * | 11/2003 | Pliley | | 81/6 |
| 6,666,866 B2 * | 12/2003 | Martz et al. | | 606/86 A |
| 6,679,914 B1 * | 1/2004 | Gabbay | | 623/14.12 |
| 6,699,252 B2 * | 3/2004 | Farr et al. | | 606/79 |
| 6,702,821 B2 * | 3/2004 | Bonutti | | 606/88 |
| 6,796,977 B2 * | 9/2004 | Yap et al. | | 606/1 |
| 6,852,114 B2 * | 2/2005 | Cerundolo | | 606/80 |
| 6,852,125 B2 * | 2/2005 | Simon et al. | | 623/16.11 |
| 6,855,165 B2 * | 2/2005 | Fell et al. | | 623/14.12 |
| 6,893,463 B2 * | 5/2005 | Fell et al. | | 623/14.12 |
| 6,923,831 B2 * | 8/2005 | Fell et al. | | 623/14.12 |
| 6,964,685 B2 * | 11/2005 | Murray et al. | | 623/13.17 |
| 6,966,928 B2 * | 11/2005 | Fell et al. | | 623/14.12 |
| 7,004,971 B2 * | 2/2006 | Serhan et al. | | 623/17.16 |
| 7,124,762 B2 * | 10/2006 | Carter et al. | | 128/898 |
| 7,163,563 B2 * | 1/2007 | Schwartz et al. | | 623/23.76 |
| 7,244,273 B2 * | 7/2007 | Pedersen et al. | | 623/14.12 |
| 7,264,634 B2 * | 9/2007 | Schmieding | | 623/14.12 |
| 7,291,169 B2 * | 11/2007 | Hodorek | | 623/14.12 |
| 7,297,161 B2 * | 11/2007 | Fell | | 623/14.12 |
| 7,338,524 B2 * | 3/2008 | Fell et al. | | 623/14.12 |
| 7,371,260 B2 * | 5/2008 | Malinin | | 623/14.12 |
| 7,462,199 B2 * | 12/2008 | Justin et al. | | 623/20.34 |
| 7,476,250 B1 * | 1/2009 | Mansmann | | 623/14.12 |
| 7,534,263 B2 * | 5/2009 | Burdulis et al. | | 623/14.12 |
| 7,575,578 B2 * | 8/2009 | Wetzler et al. | | 606/96 |
| 7,591,820 B2 * | 9/2009 | Schmieding et al. | | 606/79 |
| 7,594,922 B1 * | 9/2009 | Goble et al. | | 606/213 |
| 7,611,653 B1 * | 11/2009 | Elsner et al. | | 264/255 |
| 7,632,311 B2 * | 12/2009 | Seedhom et al. | | 623/16.11 |
| 7,641,689 B2 * | 1/2010 | Fell et al. | | 623/14.12 |
| 7,766,964 B2 * | 8/2010 | Stone et al. | | 623/13.13 |
| 7,780,668 B2 * | 8/2010 | Steiner et al. | | 606/79 |
| 7,901,457 B2 * | 3/2011 | Truncale et al. | | 623/16.11 |
| 2001/0002446 A1 * | 5/2001 | Plouhar et al. | | 623/14.12 |
| 2002/0082703 A1 * | 6/2002 | Repicci | | 623/20.29 |
| 2002/0082704 A1 * | 6/2002 | Cerundolo | | 623/20.35 |
| 2003/0036801 A1 * | 2/2003 | Schwartz et al. | | 623/23.63 |
| 2003/0229400 A1 * | 12/2003 | Masuda et al. | | 623/23.63 |
| 2003/0236573 A1 * | 12/2003 | Evans et al. | | 623/23.58 |
| 2004/0028717 A1 * | 2/2004 | Sittinger et al. | | 424/423 |
| 2004/0033212 A1 * | 2/2004 | Thomson et al. | | 424/93.7 |
| 2004/0039447 A1 * | 2/2004 | Simon et al. | | 623/13.11 |
| 2004/0044408 A1 * | 3/2004 | Hungerford et al. | | 623/13.17 |
| 2004/0062753 A1 * | 4/2004 | Rezania et al. | | 424/93.7 |
| 2004/0230303 A1 * | 11/2004 | Gomes et al. | | 623/16.11 |
| 2005/0043814 A1 * | 2/2005 | Kusanagi et al. | | 623/23.58 |
| 2005/0125077 A1 * | 6/2005 | Harmon et al. | | 623/23.72 |
| 2005/0159820 A1 * | 7/2005 | Yoshikawa et al. | | 623/23.5 |
| 2005/0196460 A1 * | 9/2005 | Malinin | | 424/548 |
| 2005/0222687 A1 * | 10/2005 | Vunjak-Novakovic et al. | | 623/23.63 |
| 2005/0251268 A1 * | 11/2005 | Truncale | | 623/23.63 |
| 2006/0030948 A1 * | 2/2006 | Manrique et al. | | 623/23.13 |
| 2006/0060209 A1 * | 3/2006 | Shepard | | 128/898 |
| 2006/0167483 A1 * | 7/2006 | Asculai et al. | | 606/151 |
| 2006/0178748 A1 * | 8/2006 | Dinger et al. | | 623/18.11 |
| 2006/0247790 A1 * | 11/2006 | McKay | | 623/23.44 |
| 2007/0014867 A1 * | 1/2007 | Kusanagi et al. | | 424/548 |
| 2007/0093896 A1 * | 4/2007 | Malinin | | 623/14.12 |
| 2007/0100450 A1 * | 5/2007 | Hodorek | | 623/14.12 |
| 2007/0113951 A1 * | 5/2007 | Huang | | 156/89.11 |
| 2007/0135917 A1 * | 6/2007 | Malinin | | 623/16.11 |
| 2007/0135918 A1 * | 6/2007 | Malinin | | 623/16.11 |
| 2007/0135928 A1 * | 6/2007 | Malinin | | 623/23.63 |
| 2007/0148242 A1 * | 6/2007 | Vilei et al. | | 424/484 |
| 2007/0179607 A1 * | 8/2007 | Hodorek et al. | | 623/14.12 |
| 2007/0185585 A1 * | 8/2007 | Bracy et al. | | 623/23.63 |
| 2007/0276506 A1 * | 11/2007 | Troxel | | 623/23.63 |
| 2008/0077251 A1 * | 3/2008 | Chen et al. | | 623/23.72 |
| 2008/0086210 A1 * | 4/2008 | Fox | | 623/14.12 |
| 2008/0125863 A1 * | 5/2008 | McKay | | 623/11.11 |
| 2008/0167716 A1 * | 7/2008 | Schwartz et al. | | 623/11.11 |
| 2008/0183291 A1 * | 7/2008 | Scheller et al. | | 623/14.12 |
| 2008/0183300 A1 * | 7/2008 | Seedhom et al. | | 623/23.76 |
| 2008/0195205 A1 * | 8/2008 | Schwartz | | 623/14.12 |
| 2008/0234820 A1 * | 9/2008 | Felt et al. | | 623/14.12 |
| 2008/0269756 A1 * | 10/2008 | Tomko et al. | | 606/87 |
| 2009/0069901 A1 * | 3/2009 | Truncale et al. | | 623/23.63 |
| 2009/0076605 A1 * | 3/2009 | Linares | | 623/14.12 |
| 2009/0076624 A1 * | 3/2009 | Rahaman et al. | | 623/23.74 |
| 2009/0088846 A1 * | 4/2009 | Myung et al. | | 623/14.12 |
| 2009/0093816 A1 * | 4/2009 | Roose et al. | | 606/87 |
| 2009/0099661 A1 * | 4/2009 | Bhattacharya et al. | | 623/17.16 |
| 2009/0131986 A1 * | 5/2009 | Lee et al. | | 606/247 |
| 2009/0306676 A1 * | 12/2009 | Lang et al. | | 606/102 |
| 2009/0312805 A1 * | 12/2009 | Lang et al. | | 606/86 R |
| 2009/0312842 A1 * | 12/2009 | Bursac et al. | | 623/23.72 |
| 2009/0319051 A9 * | 12/2009 | Nycz et al. | | 623/23.57 |
| 2010/0023015 A1 * | 1/2010 | Park | | 606/87 |
| 2010/0023127 A1 * | 1/2010 | Shohat | | 623/14.12 |
| 2010/0069910 A1 * | 3/2010 | Hasselman | | 606/87 |
| 2010/0145343 A1 * | 6/2010 | Johnson et al. | | 606/85 |
| 2010/0160914 A1 * | 6/2010 | Bastian et al. | | 606/79 |
| 2010/0168752 A1 * | 7/2010 | Edwards | | 606/87 |
| 2010/0168754 A1 * | 7/2010 | Fitz et al. | | 606/88 |
| 2010/0168857 A1 * | 7/2010 | Hatch | | 623/14.12 |
| 2010/0191242 A1 * | 7/2010 | Massoud | | 606/87 |
| 2010/0191243 A1 * | 7/2010 | Horan et al. | | 606/87 |
| 2010/0191244 A1 * | 7/2010 | White et al. | | 606/88 |
| 2010/0198224 A1 * | 8/2010 | Metzger et al. | | 606/87 |
| 2010/0228257 A1 * | 9/2010 | Bonutti | | 606/87 |
| 2010/0298894 A1 * | 11/2010 | Bojarski et al. | | 606/86 R |
| 2010/0303313 A1 * | 12/2010 | Lang et al. | | 382/128 |
| 2010/0305573 A1 * | 12/2010 | Fitz et al. | | 606/87 |
| 2010/0305574 A1 * | 12/2010 | Fitz et al. | | 606/88 |
| 2010/0305907 A1 * | 12/2010 | Fitz et al. | | 703/1 |
| 2010/0318088 A1 * | 12/2010 | Warne et al. | | 606/87 |
| 2011/0015636 A1 * | 1/2011 | Katrana et al. | | 606/87 |
| 2011/0046613 A1 * | 2/2011 | Schmitz et al. | | 606/1 |

* cited by examiner

INSTRUMENTATION AND METHOD FOR REPAIR OF MENISCUS TISSUE

RELATED APPLICATION

This application claims the benefit of Provisional Application No. 61/064,461, filed Mar. 6, 2008.

FIELD OF INVENTION

The present invention relates to the field of treatment of injured human knee joints, and in particular, to replacement and repair of a damaged human knee joint meniscus using a substantially immunologically compatible allograft meniscus.

The present invention is generally directed toward a method and instrumentation to replace a damaged human knee joint meniscus with an allograft meniscus.

BACKGROUND OF THE INVENTION

The human knee is a complex joint containing spatially interrelated bones, ligaments, and cartilaginous structures which interact to create a variety of motions. Specifically, the femoral condyles articulate with the surface plateaus of the tibia, through the cartilaginous medial and lateral menisci, and all of these structures are held in place by various ligaments. Undamaged menisci provide shock absorption for the knee by ensuring proper force distribution, stabilization, and lubrication for the interacting bone surfaces within the knee joint, which are routinely exposed to repeated compression loading during normal activity. Much of the shock absorbing function of the medial and lateral menisci is derived from the elastic properties inherent to cartilage.

The meniscus of the knee joint is a half moon shaped piece of cartilage that lies between the weight bearing joint surfaces of the femur and the tibia. It is triangular in cross section and is attached to the lining of the knee joint along its periphery. There are two menisci in a normal knee; the outer one is called the lateral meniscus, the inner one the medial meniscus. The menisci play an important role in absorbing impact loads.

The menisci provide stability to the knee joint. Either of the menisci may tear or split when subjected to certain forces. This injury, which is commonly referred to as torn cartilage in the knee, is painful and may limit mobility.

Undamaged menisci provide shock absorption for the knee by ensuring proper force distribution, stabilization, and lubrication for the interacting bone surfaces within the knee joint, which are routinely exposed to repeated compression loading during normal activity. Much of the shock absorbing function of the medial and lateral menisci is derived from the elastic properties inherent to cartilage. When menisci are damaged through injury, disease, or inflammation, arthritic changes occur in the knee joint, with consequent loss of function.

The meniscus, a cartilaginous tissue, performs several functions in the knee including load transmission from the femur to the tibia, stabilization in the anterior-posterior position during flexion, and joint lubrication. Damage to the meniscus results in reduced knee stability and knee locking. Over 20 years ago, meniscectomies were performed which permitted pain relief, but were subsequently found to induce the early onset of osteoarthritis.

Injury to the knee involving a tear in the meniscus is a common occurrence, often occurring in the context of athletic events, and is prevalent in the younger population. The meniscus is recognized as being vital to the biomechanical stability and protection of the knee joint. Damage to the meniscus can greatly increase the likelihood of the articular surfaces of the knee joint developing conditions such as osteoarthritis. A common remedy which has been previously used for tears in the meniscus involved removal of the meniscus. However, it has been shown that degenerative changes in the knee are directly proportional to the amount of meniscus removed. Thus, in many instances it is desirable to repair the torn meniscus with the objective being to prevent instability of the knee joint and to prevent onset of conditions such as osteoarthritis.

Of the approximately 600,000 meniscal injuries that occur annually in the United States, an estimated 80% of tears are located in the avascular, irreparable zone. Thus instrumentation and a method that repairs "non-repairable" tears by replacement of the damaged meniscus with an allograft implant would be valuable for painless musculoskeletal movement and prevention of the early onset of osteoarthritis in a large segment of the population.

Various repairs and replacements have been used to relieve pain and restore function to the joint where the cartilage has been damaged. For example hyaline cartilage may be damaged by impact injuries or worn down in the course of arthritis. Typically, the ends of the bones forming a joint are cut away and replaced with prosthetic bearings made of metal and plastic to restore pain free articulation of the joint. In cases where the damage occurs as a small localized defect, some investigators have attempted to replace only the small defect by placing a patch of replacement material, natural or synthetic, at the defect.

Current methods for repairing tears in the meniscus are technically very challenging for the surgeon. One widely used technique requires that a long needle with a suture be passed through the torn meniscus and the knee joint. The needle carrying the suture is passed through the meniscus and the knee in its entirety several times until the meniscal tear is closed. As this procedure is typically performed arthroscopically, the amount of space available within the knee for manipulating the long needle through the meniscus is extremely limited. The procedure often requires more than one pair of hands, with one pair inserting the needle into the knee while another pair uses graspers, operating in the limited inflated space in the interior of the knee, to shuttle the needle through the meniscus and out the other side of the knee.

One area of meniscal repair is the use of allograft meniscal tissue used as an implant replacement for the damaged meniscus. U.S. Pat. No. 7,124,762 issued Oct. 24, 2006 discloses a meniscus allograft with an integral bone bridge. The bone bridge is held in a clamp and trimmed with a surgical saw so that it fits into a trapezoidal shaped or dovetail shaped blind end groove cut into the upper surface of the tibia. A rasp is used to create the orthogonal angle of the dovetail transplant.

This type of meniscal allograft transplant is currently being used by Arthrex, Inc. A similar allograft implant having a rectangular bone bridge is trimmed on a cutting board so that the bridge fits into a rectangular groove cut into the tibial surface is used by the Stryker corporation. The rectangular slot on the tibular surface is lined and a hole is drilled parallel to the marker line with the groove being formed by a rasp. The allograft implant and instruments and method of transplantation are shown in U.S. Pat. No. 6,699,252 issued Mar. 2, 2004. A double bone plug meniscus surgical technique is utilized by Cryolife, Inc. with cylindrical bone plugs cut on each end of the horns of the allograft meniscus which are placed in cylindrical blind bores cut into the tibial surface, and held in place by sutures.

Another reference is U.S. Pat. No. 5,092,894 issued Mar. 3, 1992 which discloses a biocompatible meniscus implant constructed of deformable and resilient material with the horns of the meniscus being mounted in tubing which is inserted into cylindrical bores cut into the tibia.

A number of meniscus prostheses have been devised which employ resilient materials such as silicone rubber or natural rubber, as in U.S. Pat. No. 4,344,193 (issued Aug. 17, 1982) and U.S. Pat. No. 4,502,161 (issued Mar. 5, 1985). Meniscal cutting devices have been disclosed in U.S. Pat. No. 4,711,238 (issued Dec. 8, 1987).

SUMMARY OF THE INVENTION

The present invention provides a substantially non-immunogenic meniscal cartilage allograft implant for implantation into a human in need of knee meniscus repair and an instrument kit for the surgeon to accomplish the implant.

The present invention is directed to a method and a kit including an allograft implant and instrumentation to surgically replace a damaged human knee joint meniscus with an allograft meniscus.

It is also an object of the invention to provide a pre-machined allograft meniscus structure having a bone base connecting the horns of the meniscus which can be mounted and fastened to a tibial surface.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

DETAILED DESCRIPTION OF THE INVENTION

The preferred embodiment and best mode of the present invention is shown in FIGS. 1 through 10

Figure 1:
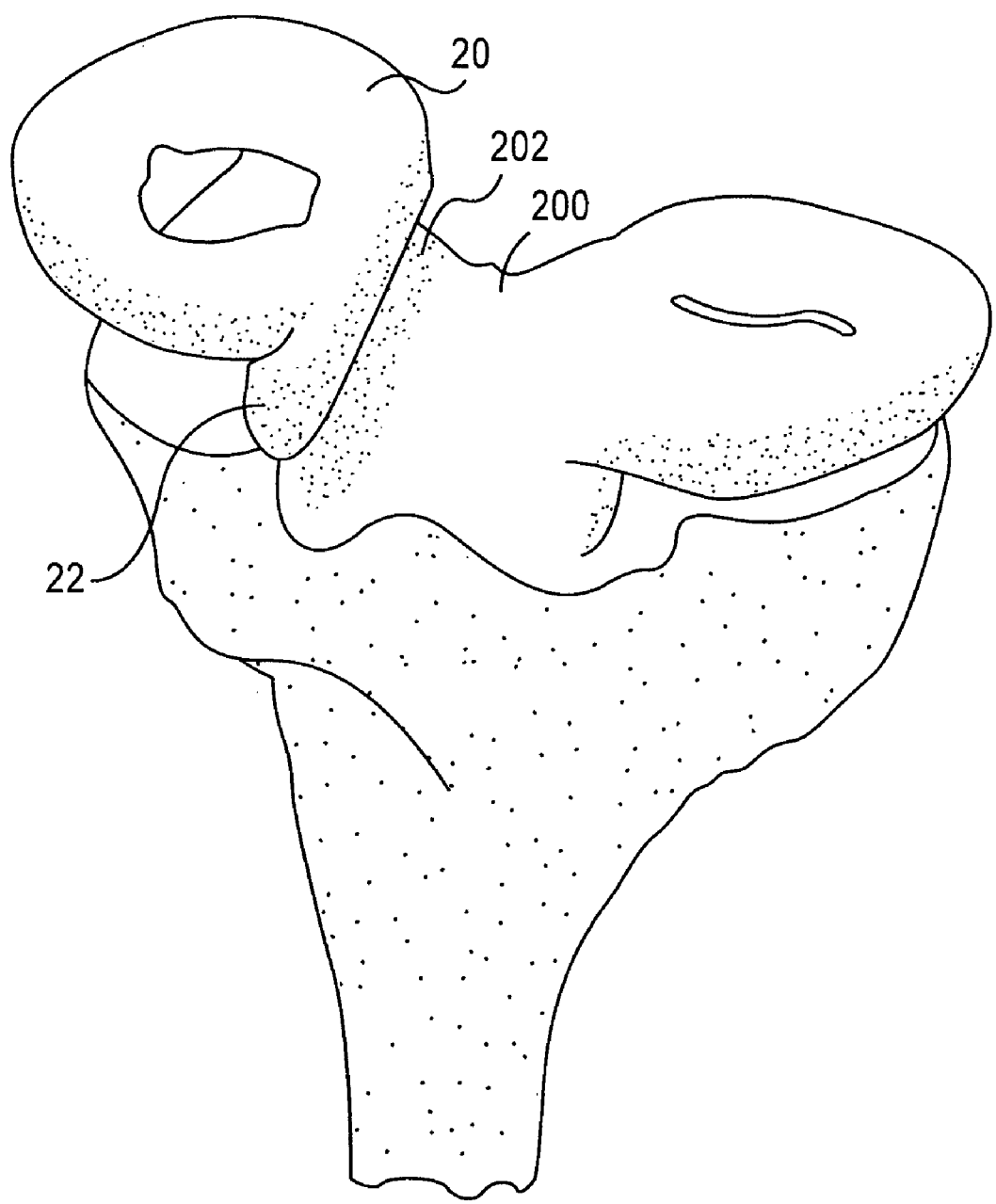
FIG. 1 is a perspective view of the allograft meniscus implant prior to mounting in the tibial groove.
Figure 11:
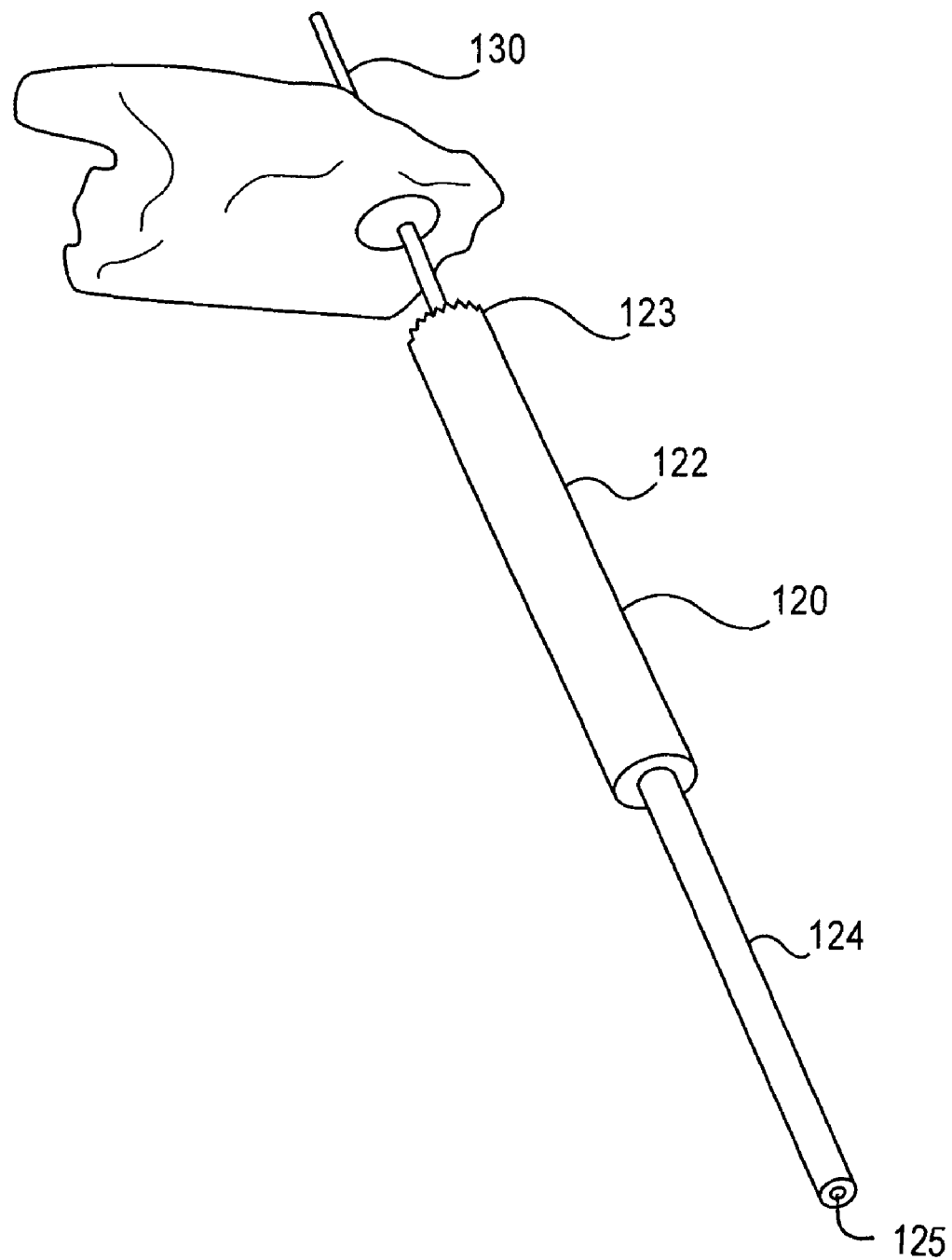
FIG. 11 is a perspective view of the circular cutting saw used for an alternative embodiment; and, FIG. 12 is an enlarged detailed perspective partial view of the cutting blade of an alternative meniscus implant embodiment.
Figure 12:
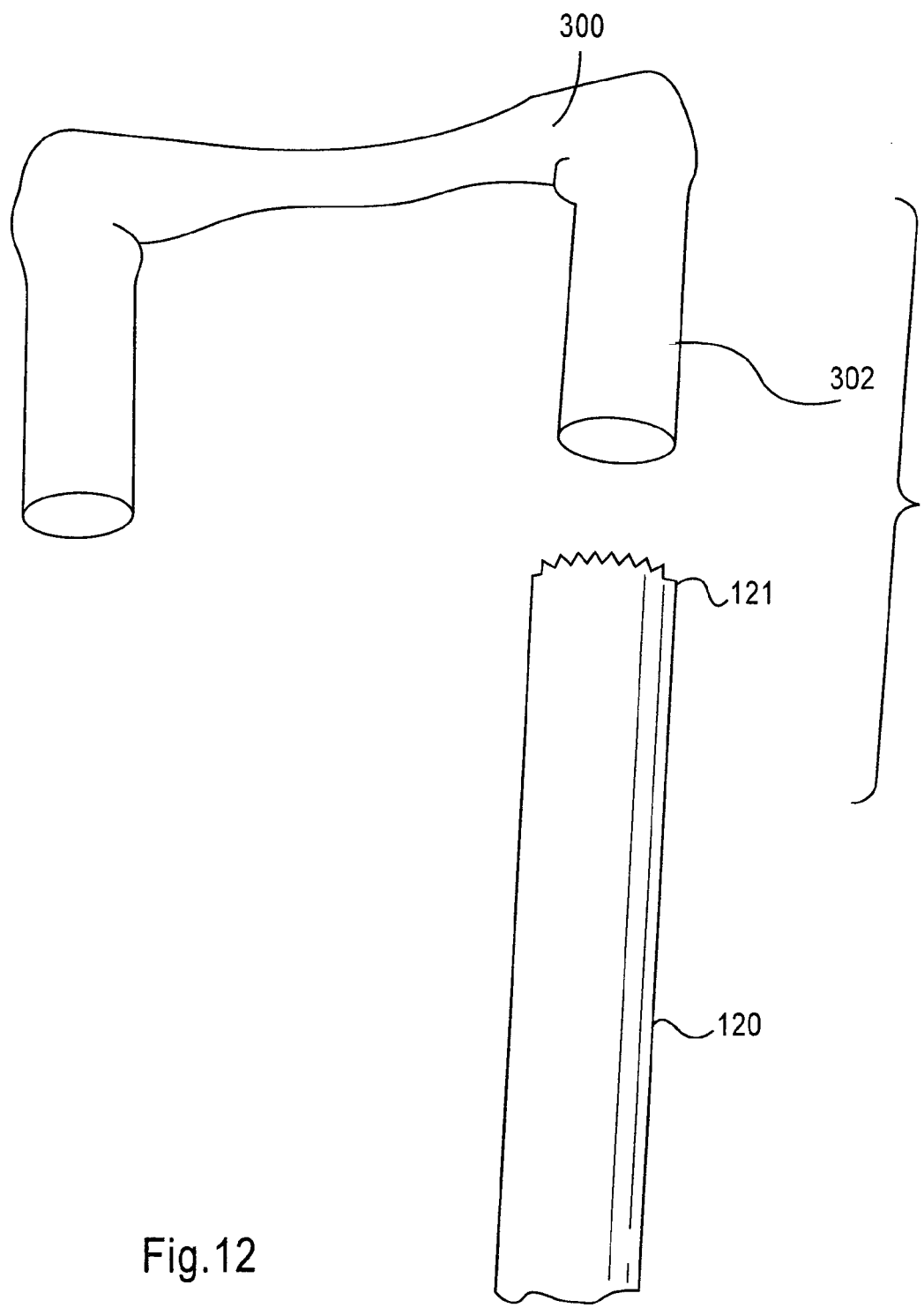

As shown in the drawings, an allograft meniscus implant 20 utilizing a bone base 22 is shown mounted in groove 202 of tibia 200 as is shown in FIG. 1 in accordance with the present invention. Another embodiment in an allograft meniscus 300 having circular posts 302 is shown in FIGS. 11 and 12.

The surface of bone base can be modified by acid treatment to remove a layer of the inorganic, mineral material in such a way as to leave the mechanical properties substantially unchanged or to provide a construct having suitable compression and bending strength. This allows the addition of BMP's and other desirable additives which are more fully set forth herein to be introduced to the surface and thereby enhance the healing rate of the cortical bone in surgical procedures. The process also exposes the naturally occurring BMP's near the surface and renders the surface with biological properties similar to fully demineralized bone (DMB). The inner mass of the bone construct would be left intact to contain the naturally occurring BMP's.

The feature of the bone base that make it desirable as a surgical material are, its ability to slowly resorb and be integrated into the space it occupies while allowing the bodies own healing mechanism to restore the repairing bone to its natural shape and function by a mechanism known in the art as creeping substitution.

Figure 2:
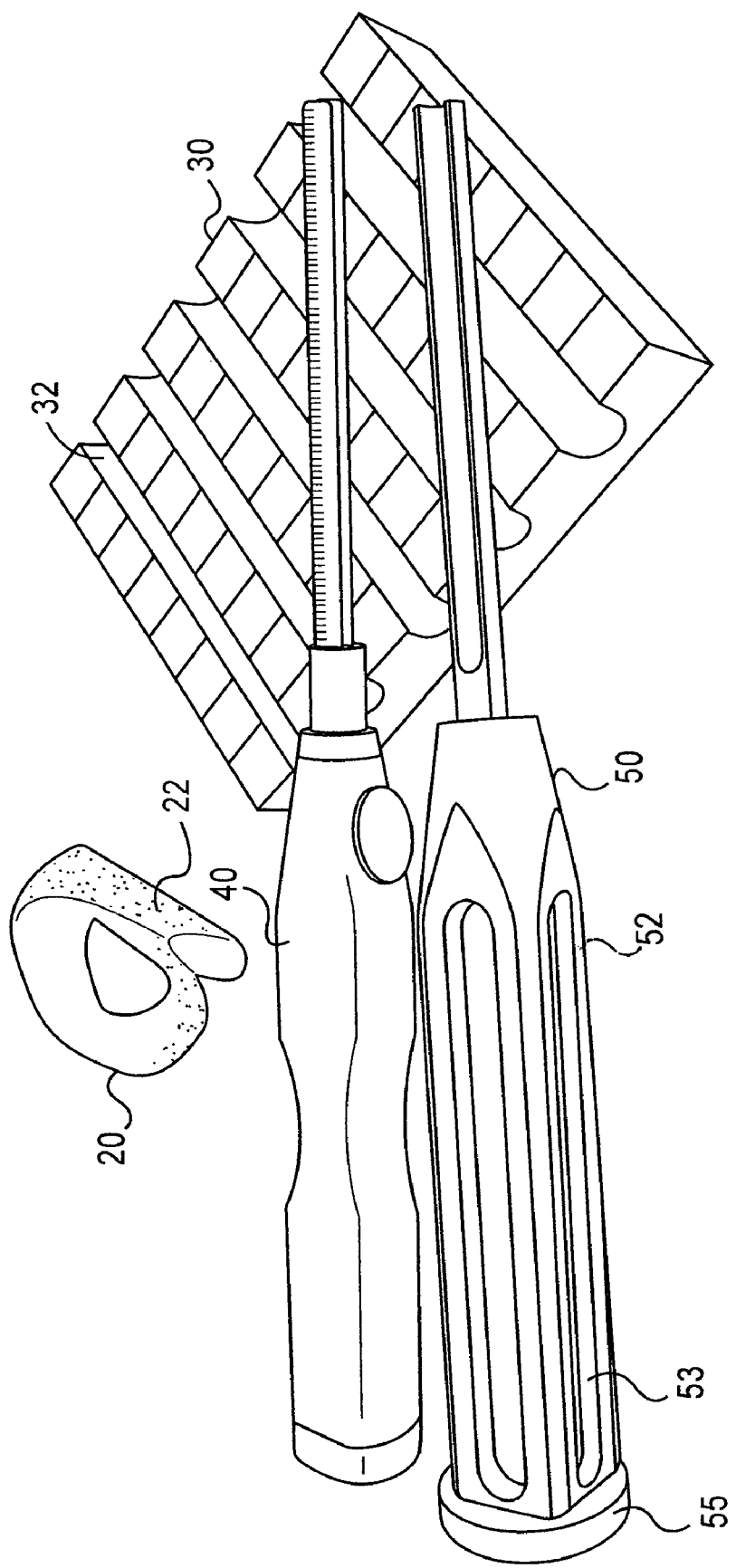
FIG. 2 is a perspective view of the implant, gauge, tissue chisel, and meniscal base sizing block.
Figure 9:
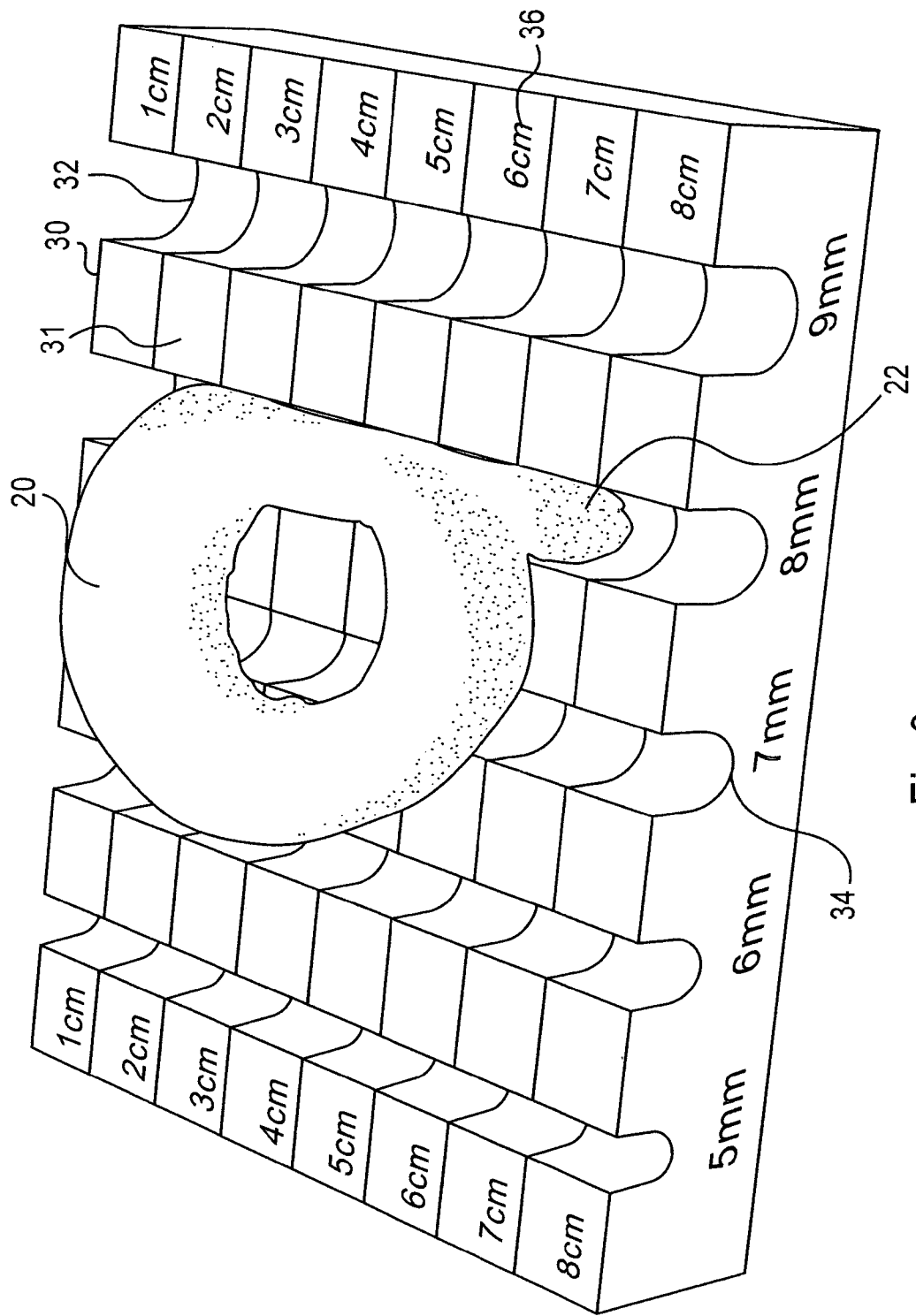
FIG. 9 is an enlarged perspective view of the sizing block with an allograft meniscus implant base placed in a sizing groove.

The allograft meniscus implant 20 is prepared with the use of an instrument kit comprising a sizing block 30 which allows the base to be sized, a hand gauge device 40, a tissue chisel 50, a clamping drill 60 and a cutting miter block 100. The sizing block 30 which is best shown in FIGS. 2 and 9 is in the form of a stainless steel block 30 defining a plurality of parallel grooves 32 having different widths ranging from 5 mm to 9 mm with the grooves having a rounded base 34. It is of course noted that greater or lesser widths can formed in the block as desired. Marking indicia 36 is etched, painted or cut on the upper planar face surface 31 to allow the user to ascertain the length of the base of the implant 20 so that the same can be placed in the groove 202 cut into the tibia 200.

Figure 3:
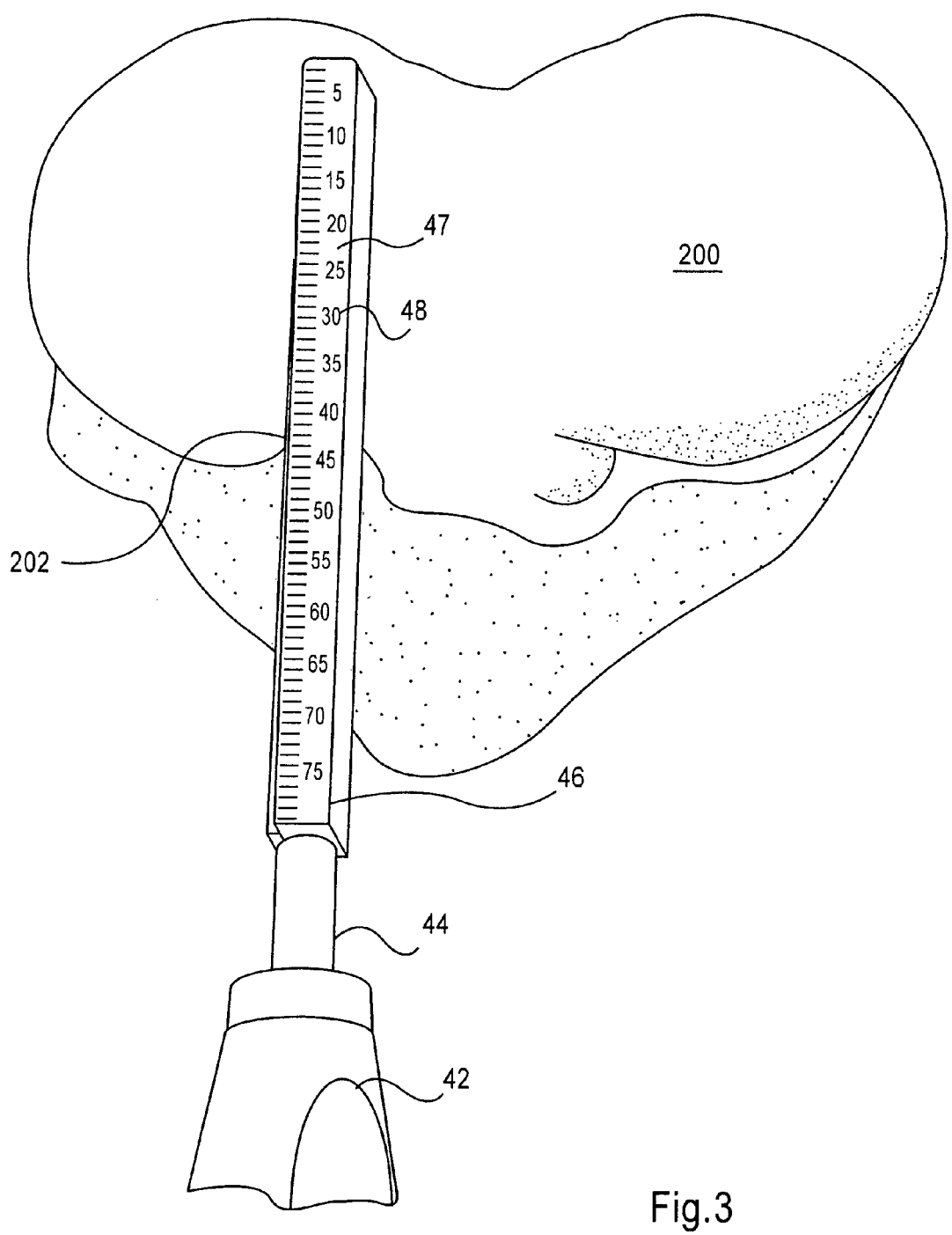
FIG. 3 is a an enlarged perspective view of the gauge in an exemplary tibial head.

A gauge 40 as shown in FIGS. 2 and 3 is used to measure the length of the groove 202 cut into the tibia 200. The gauge 40 is constructed with a handle 42 ergonomically formed to conform to the hand of a user, a stem member 44 mounted to the handle 42 which holds the linear gauge portion 46 and marking indicia 48 which is printed on the planar surface 47 of the gauge portion 46. The marking indicia may be etched painted or cut into the surface 47. This measures the length of the groove 202 in the tibia 200.

Figure 4:
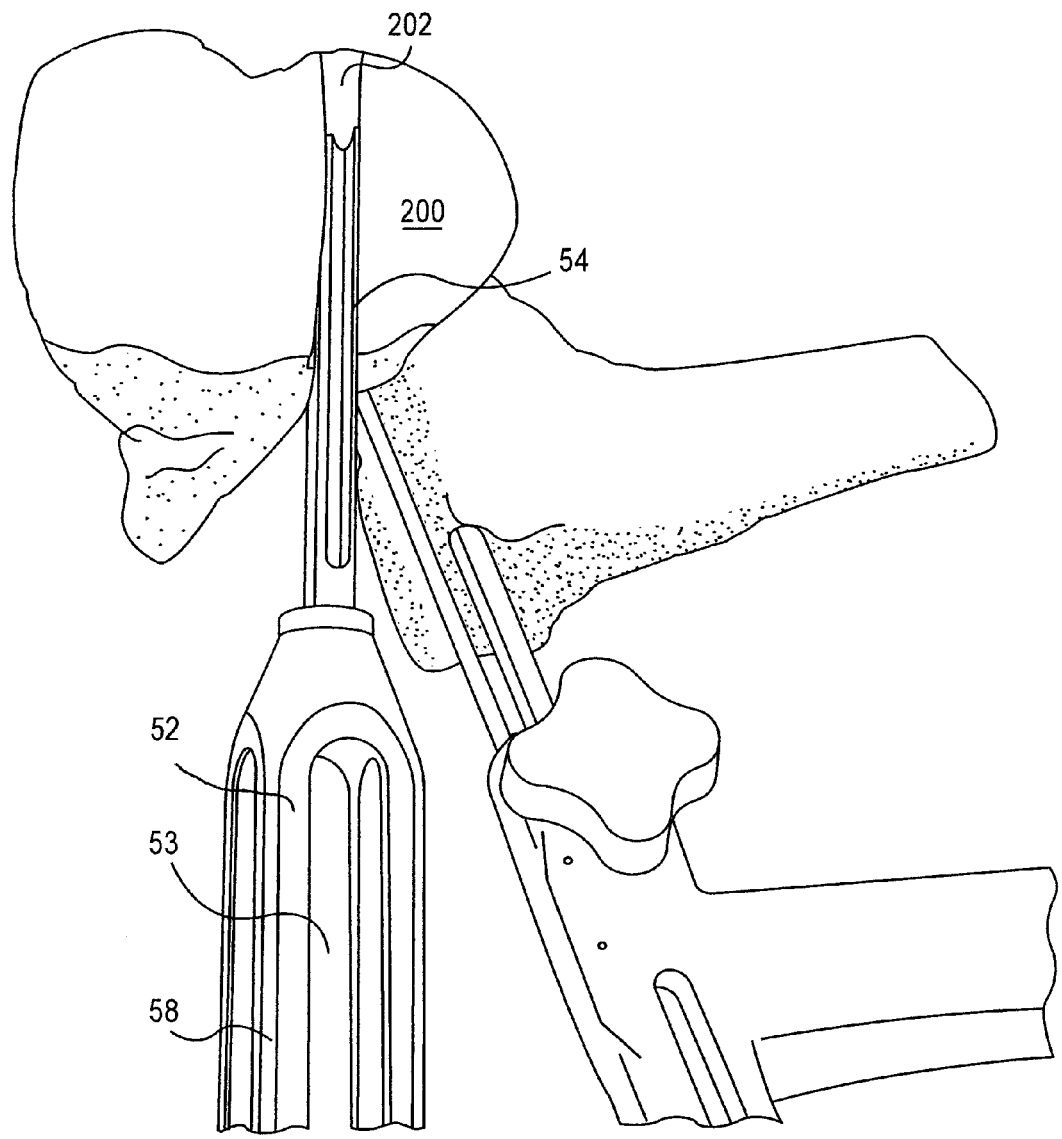
FIG. 4 is a perspective partial view of tissue chisel and tissue drill in engagement with the tibial head.
Figure 5:
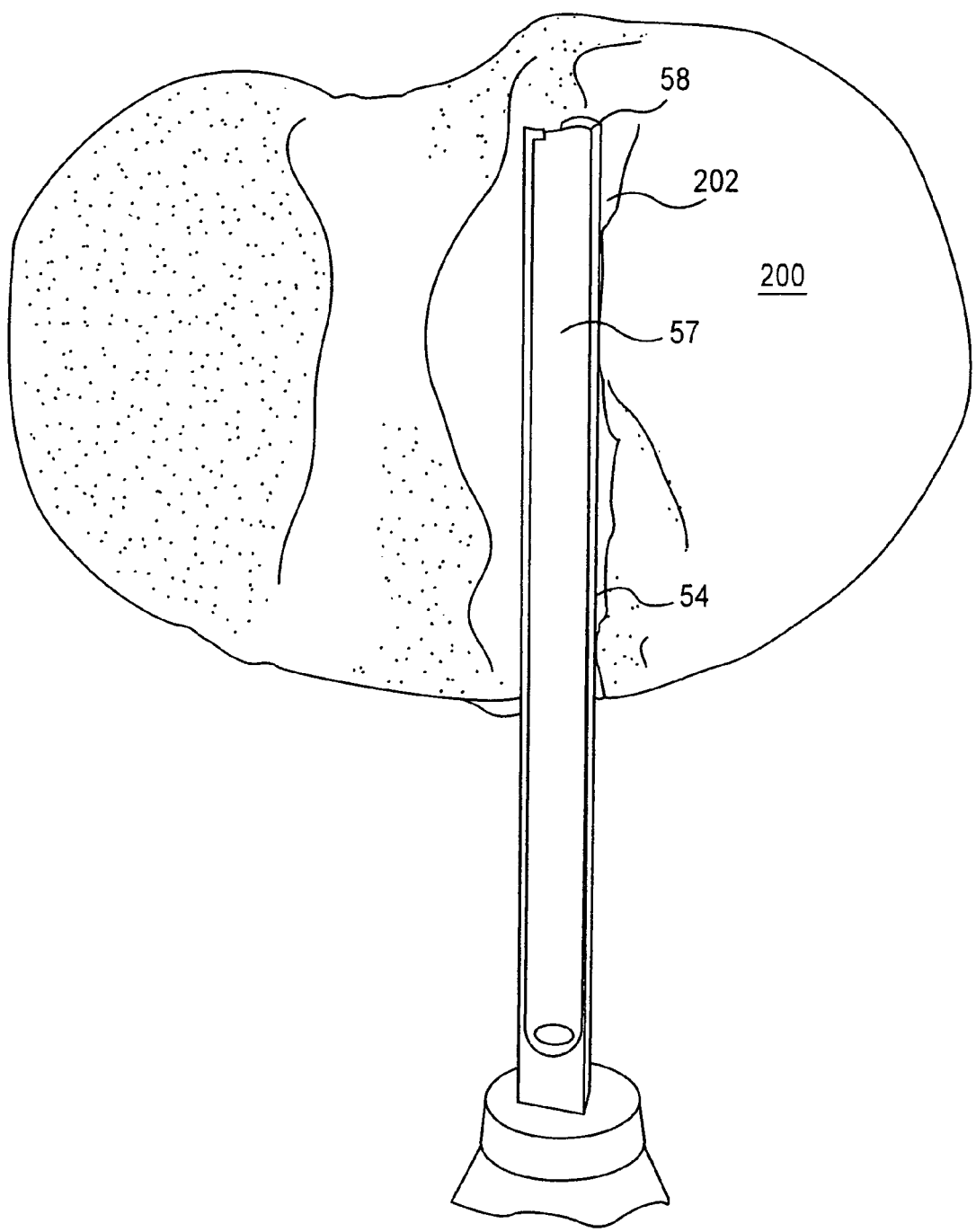
FIG. 5 is an enlarged top plan view of the tissue chisel cutting blade.

A tissue chisel 50 as shown in FIGS. 2, 4 and 5 is used to cut the groove 202 into final shape once the bone has been drilled with an initial depth bore and a centering pin inserted. The tissue chisel rides on the centering pin to provide a uniform groove cut. The tissue chisel is constructed with a stainless steel handle 52 which is formed with linear through going slots 53 and a solid circular striker end 55 with a planar end surface which receives the impact of a hammer. A cutting blade 54 having a predetermined width which corresponds to the width of the base bone 22 of the implant is mounted to the handle 52. The cutting blade has a linear cutout portion 54 which runs to the distal end 58 of the cutting blade which is beveled.

Figure 6:
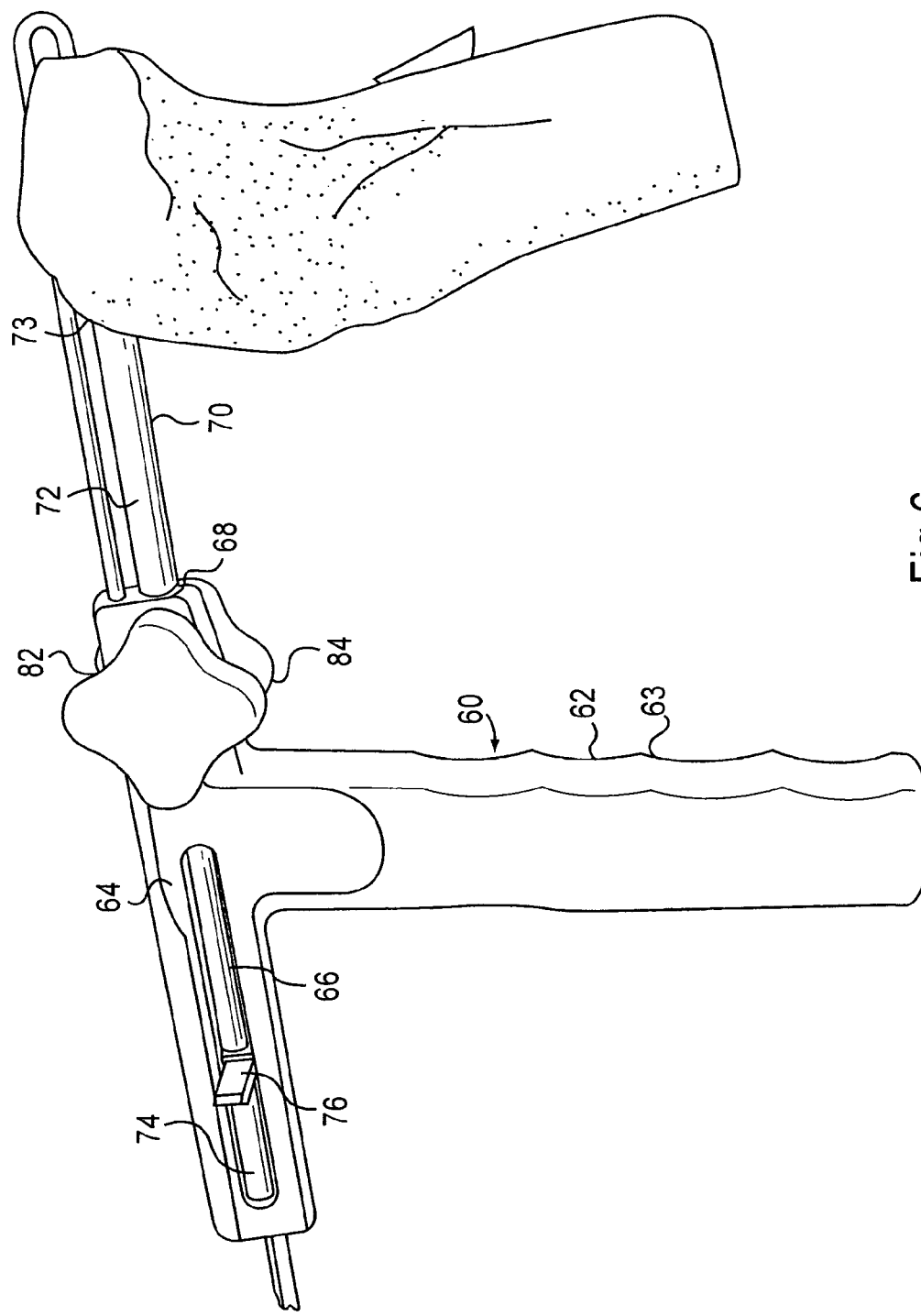
FIG. 6 is side elevation view of the tissue drill.
Figure 7:
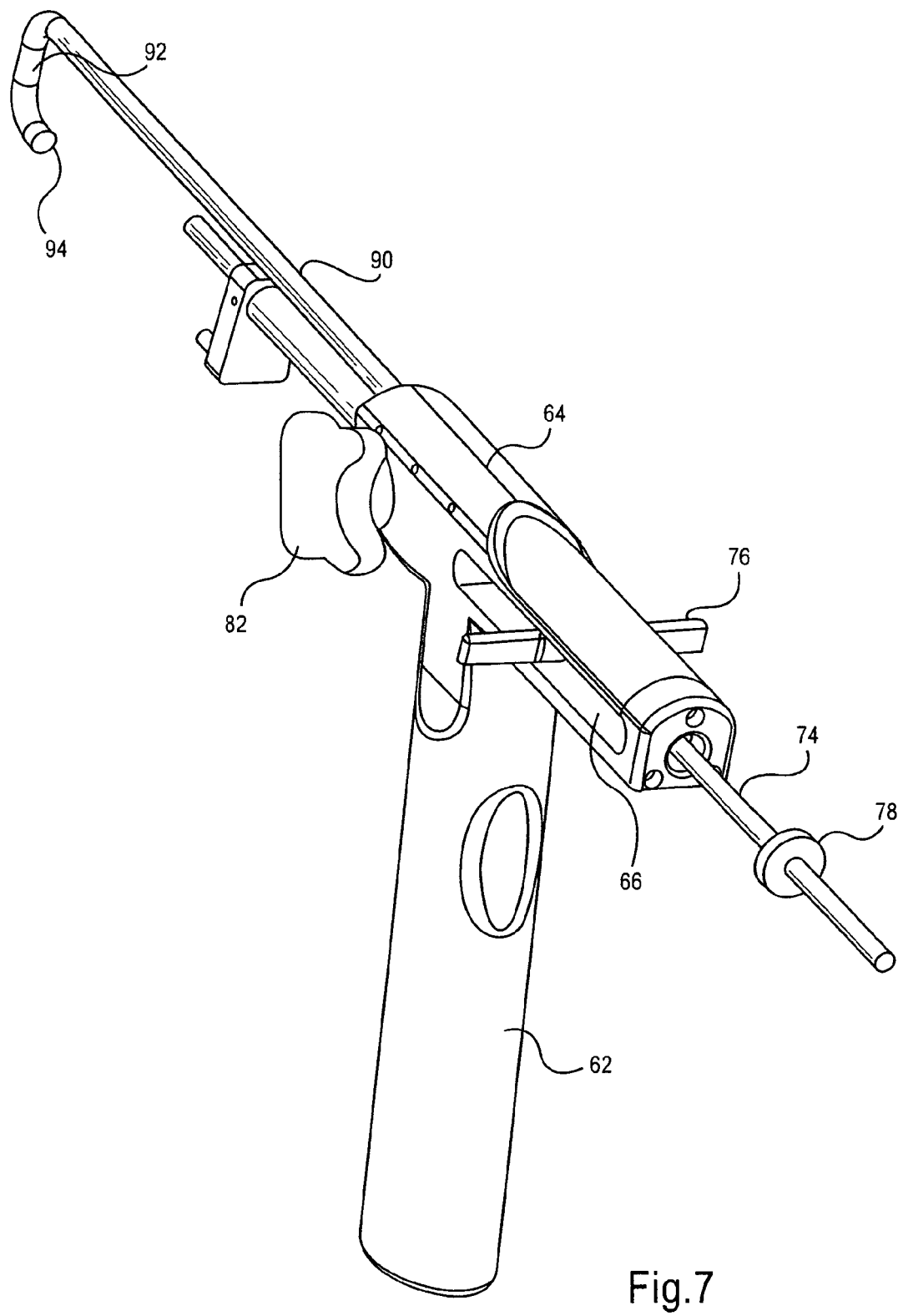
FIG. 7 is a rear perspective view of the tissue drill.
Figure 8:
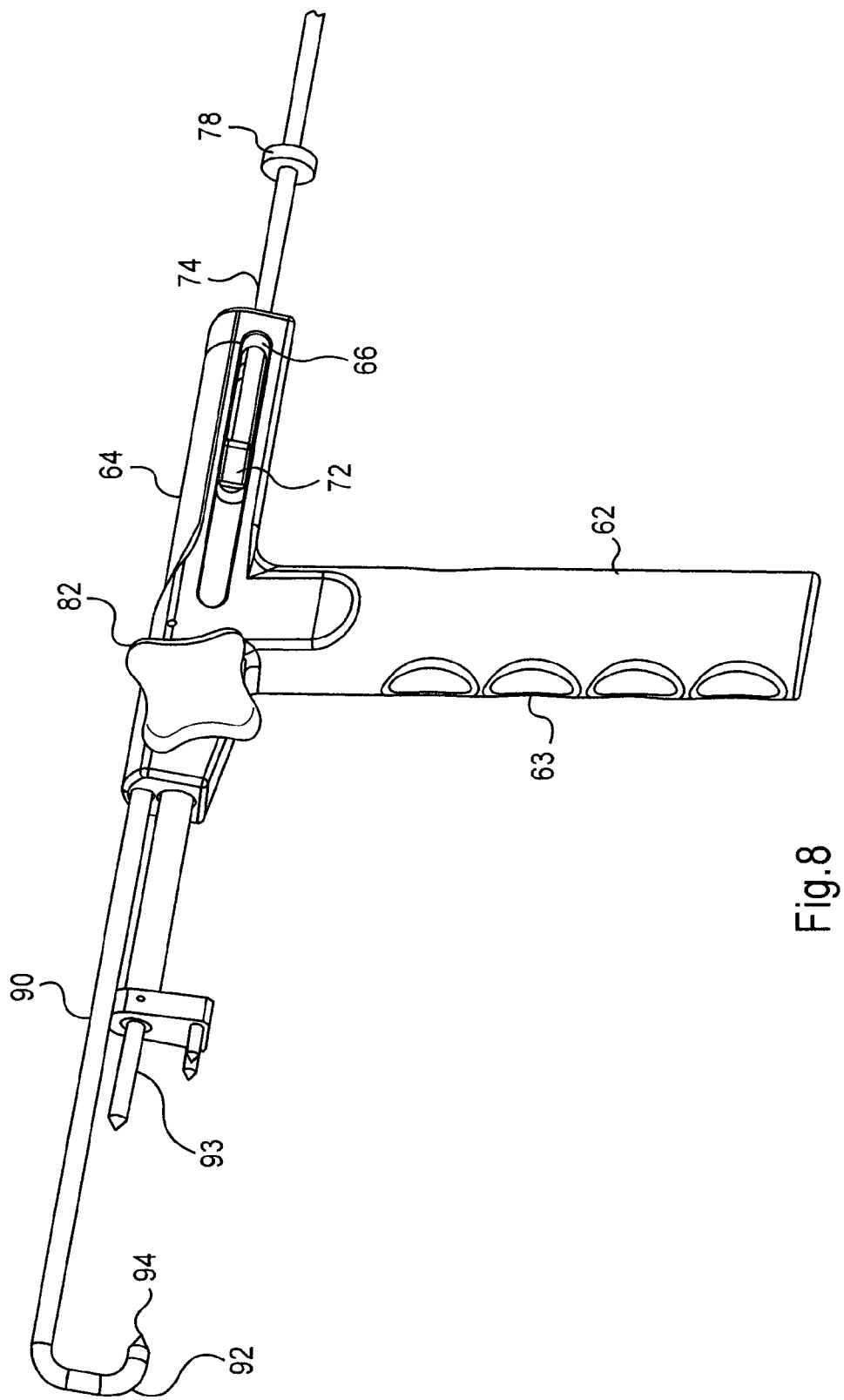
FIG. 8 is a perspective view of the tissue drill.

A drill mechanism 60 as shown in FIGS. 6-8 is constructed with a pistol type grip handle 62 having undulating grip segments 63 and a drill housing 64 integrally formed with the handle 62. The drill housing 64 defines a through going slot 66 along its sides and has a central through going bore 68 which holds the drill bit assembly 70. The drill bit assembly 70 has a distal portion 72 with a pointed end 73 which engages the tibia and drills a bore into the tibia a desired length and a rear portion 74 formed with outwardly extending arms 76 which extend through slots 66. The arms 76 are used to manually position the drill bit against the tibia forcing the tibia against the fixed clamp arm 94. It is envisioned that the drill will have a trigger (not shown) which will engage a ratchet drive to drive the drill bit forward with each pull of the trigger. The rear portion 74 of the drill bit is cylindrical and has a diameter less than the distal portion 72 and is formed with a circular stop 78 which limits the forward movement of the drill bit. A locking mechanism 82 in the form of a thumb screw with an external handle 84 is mounted to the housing and is adapted to engage the drill bit assembly to hold the same in a clamping position. A fixed clamp arm 90 is mounted to the housing 64 above the drill bit. The clamp arm 90 has a distal end 92 forming a C clamp and the end 94 is formed with a conical point. After the drill has been activated and a blind bore formed in the tibia, a centering pin is inserted into the bore so that the cutting chisel 50 is positioned for a uniform cut as to depth and length.

Figure 10:
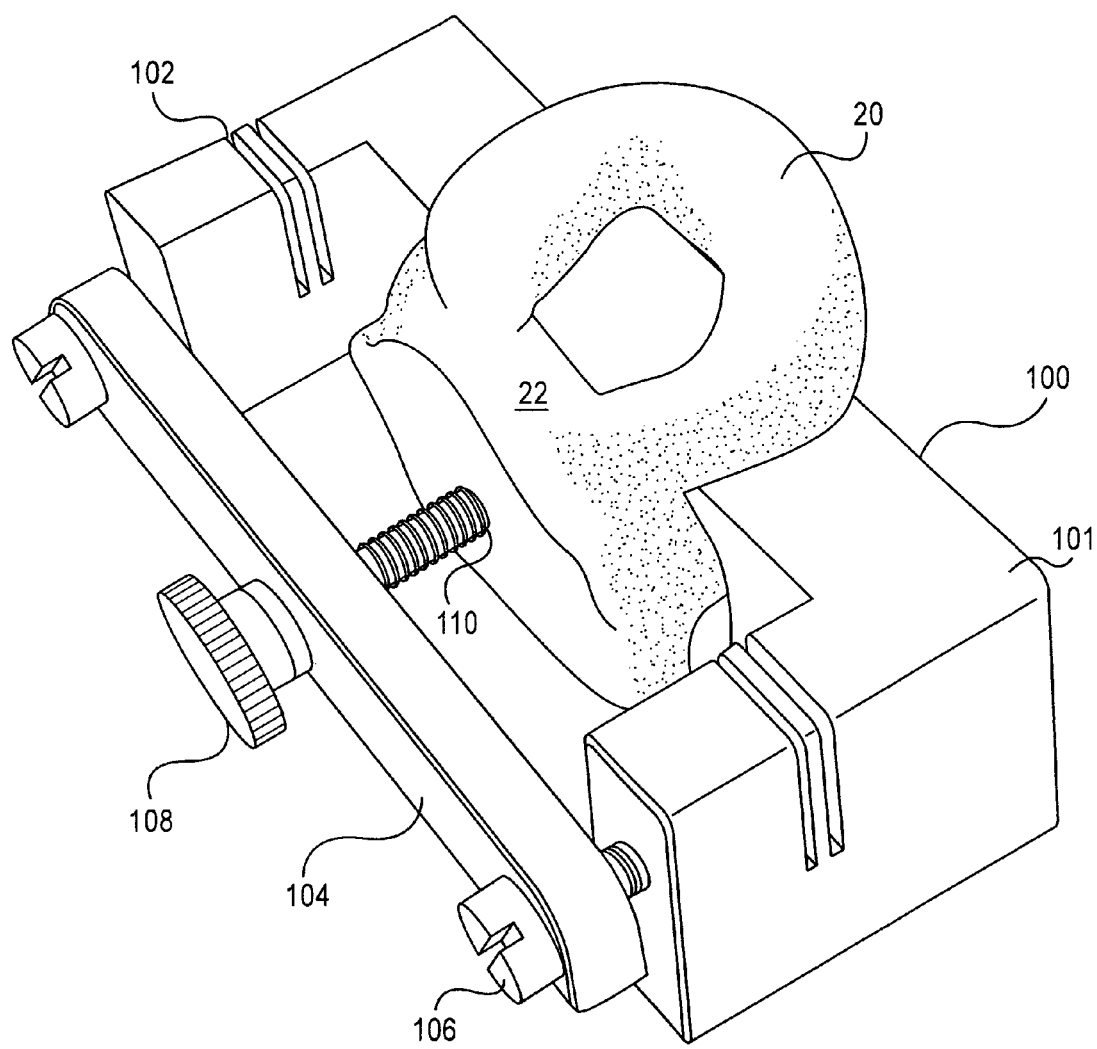
FIG. 10 is an enlarged perspective view of the cutting block with allograft meniscus implant mounted therein.

A cutting workstation 100 as shown in FIG. 10 is constructed with a C shaped housing 101 defining a plurality of parallel aligned cutting slits 102 in each arm which are adapted to receive a saw blade of standard construction to trim the meniscus bone base to a desired size to fit into a groove 202 as shown in FIG. 1. A clamp bar 104 is mounted to the housing 101 by screws 106 and a threaded thumb screw 108 is mounted to the clamp bar 104 and is adapted to rotate in the clamp bar so that the distal end 110 of the thumb screw engages the bone base of the implant 20.

In operation the implant 20 has its bone base cut to a desired width in workstation 100. The finished base is measured in the sizing groove of the sizing block 30 for width and length. The tibia is then drilled with drill 60 to the appropriate depth and length and groove 202 is formed in the tibia with the tissue chisel 50 so that the width is the same as the width of the bone base. The bone base is press fit into the groove 202 and may be secured with a bone screw.

Another embodiment is shown in FIGS. 11 and 12. In this embodiment the bone base is cut away leaving two cylindrical bone posts 302 which are pulled by sutures into bores drilled by a circular saw into the tibia. The posts 302 can be held in place in the bores (not shown) by sutures. The posts 302 are cut by a circular saw 120 having a hollow barrel 122 with cutting teeth 123 around the distal periphery of the barrel.

The shank 124 of the saw has a central axial through going bore 125 which receives a centering pin 130 which has previously been inserted into the implant as is shown in FIG. 11. The shank 124 can be received in a drill bit for circular rotation.

It is well known that bone contains osteoinductive elements known as bone morphogenetic proteins (BMP). These BMP's are present within the compound structure of cortical bone and are present at a very low concentrations, e.g. 0.003%. The BMP's are present in higher concentrations in cancellous bone. BMP's direct the differentiation of pluripotential mesenchymal cells into osteoprogenitor cells which form osteoblasts. The ability of freeze dried demineralized bone to facilitate this bone induction principle using BMP present in the bone is well known in the art. However, the amount of BMP varies in the bone depending on the age of the bone donor and the bone processing.

It is also possible to add one or more rhBMP's to the bone by soaking and being able to use a significantly lower concentration of the rare and expensive recombinant human BMP to achieve the same acceleration of biointegration. The addition of other useful treatment agents such as vitamins, hormones, antibiotics, antiviral and other therapeutic agents could also be added to the bone.

Any number of medically useful substances can be incorporated in the bone block and meniscus assembly by adding the substances to the assembly. Such substances include collagen and insoluble collagen derivatives, hydroxyapatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin, gentamycin and silver salts. It is also envisioned that amino acids, peptides, vitamins, co-factors for protein synthesis; hormones; endocrine tissue or tissue fragments; synthesizers; enzymes such as collagenase, peptidases, oxidases; polymer cellpl scaffolds with parenchymal cells; angiogenic drugs and polymeric carriers containing such drugs; collagen lattices; biocompatible surface active agents, antigenic agents; cytoskeletal agents; cartilage fragments, living cells, cell elements such as chondrocytes, red blood cells, white blood cells, platelets, blood plasma, bone marrow cells, mesenchymal stem cells, pluripotential cells, osteoblasts, osteoclasts, fibroblasts, epithelial cells and entothial cells, natural extracts, tissue transplants, bioadhesives, transforming growth factor (TGF-beta), insulin growth factor (IGF-1), platelet derived growth factor (PDGF), fibroblast growth factor (FGF)(Numbers 1-23), platelet derived growth factor (PDGF), vascular endothelial growth factor (VEGF), osteopontin; growth hormones such as somatotropin; cellular attractants and attachment agents; fibronectin; immuno-suppressants; permeation enhancers, e.g. fatty acid esters such as laureate, myristate and stearate monoesters of polyethylene glycol, enamine derivatives, alpha-keto aldehydes can be added to the composition.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A kit for placing an allograft meniscus implant on the surface of a human tibia comprising (a) a drill apparatus, (b) a cutting instrument, (c) a meniscus bone base measuring block mechanism and (d) a cutting work station with a unitary C-shaped body and a cross bar mounted to legs of said C-shaped body, a thumb screw with a threaded shank is threadably mounted to said crossbar, said shank extending through said crossbar with a distal end of said thumb screw shank being adapted to engage a meniscus implant to secure said meniscus implant in a fixed position in said cutting work station.

2. A kit as claimed in claim 1 including a hand gauge provided with marking indicia along its length.

3. A kit as claimed in claim 1 wherein said drill apparatus comprises a housing with an integral handle extending from said housing, a drill rod assembly axially and rotatably mounted in said housing and a clamping rod mounted in said housing and extending past said housing, said clamping rod having a C shaped end curved back towards said housing.

4. A kit as claimed in claim 3 wherein said drill apparatus handle is a pistol type grip.

5. A kit as claimed in claim 1 including a circular core saw.

6. A kit for placing an allograft meniscus implant on the surface of a human tibia comprising a meniscal implant of allograft material and a plurality of instruments comprising (a) a drill apparatus, (b) a chisel, (c) a meniscus bone base measuring block and (d) a cutting work station, said bone base measuring block defining a plurality of parallel grooves, each of which has a different width and marking indicia placed along the length of said grooves, said cutting workstation has a C shaped body with the legs defining a plurality of aligned slits and a cross bar mounted to said legs, and a thumb screw threadably mounted to said cross bar.

7. A kit as claimed in claim 6 wherein said drill apparatus comprises a housing with a handle extending from said housing, a drill rod assembly axially and rotatably mounted in said housing and a clamping rod mounted in said housing and extending away from said housing, said clamping rod having a C shaped end curved back towards said housing.

8. A kit as claimed in claim 6 wherein said allograft meniscus implant has a bone base connecting the ends of said meniscus implant.

9. A kit as claimed in claim 6 wherein said allograft meniscus implant has cylindrical plugs at each end of said meniscus implant.

10. A kit as claimed in claim 6 including a hand gauge provided with marking indicia along its length.

11. A kit for placing an allograft meniscus implant on the surface of a human tibia comprising a meniscal implant of allograft material including a bone base and a plurality of instruments comprising (a) a drill apparatus, (b) a chisel, (c) a meniscus bone base measuring block and (d) a cutting work station, said bone base measuring block defining a plurality of parallel grooves, each of which has a different width and marking indicia placed along the length of said grooves, said cutting workstation has a C shaped body with the legs defining a plurality of aligned slits and a cross bar mounted to said legs, a thumb screw threadably mounted to said cross bar, said drill apparatus comprises a housing with an integral handle extending from said handle, a drill rod assembly axially and rotatably mounted in said housing and a clamping rod mounted in said housing and extending past said housing, said clamping rod having a C shaped end curved back towards said housing.

12. A kit for placing an allograft meniscus implant on the surface of a human tibia comprising a meniscal implant of allograft material including a bone base and instrumentation comprising (a) a drill apparatus, (b) a chisel, (c) a meniscus bone measuring block, said bone measuring block defining a plurality of parallel grooves, each of said grooves having a different width and marking indicia placed along the length of said grooves and (d) a cutting work station.

13. A kit as claimed in claim 12 wherein said chisel has a handle formed with linear throughgoing slots and a circular strike end, a cutting blade is mounted to said handle on an end opposite said circular strike end, said cutting blade defining a linear cutout portion.

14. A kit as claimed in claimed 13 wherein said cutting blade has a distal beveled end.

* * * * *